US009881212B2

(12) United States Patent
Solano Ferrández et al.

(10) Patent No.: US 9,881,212 B2
(45) Date of Patent: Jan. 30, 2018

(54) INFRARED IMAGE BASED EARLY DETECTION OF OIL SPILLS IN WATER

(75) Inventors: José Vicente Solano Ferrández, Arroyomolinos (ES); Ivana Daniela Esposito Cassiba, Amsterdam (NL); Marcos García Caravantes, Madrid (ES); Juan Pablo Gómez González, Alcala de Henares (ES); Javier Rodriguez Martín De Los Santos, Torrejon de Ardoz (ES); Ignacio Miñambres Chamorro, Torrejon de Ardoz (ES)

(73) Assignees: REPSOL, S.A., Madrid (ES); INDRA SISTEMAS, S.A., Madrid (ES)

( * ) Notice: Subject to any disclaimer, the term of this patent is extended or adjusted under 35 U.S.C. 154(b) by 0 days.

(21) Appl. No.: 14/412,384

(22) PCT Filed: Jul. 4, 2012

(86) PCT No.: PCT/ES2012/070494
§ 371 (c)(1),
(2), (4) Date: Apr. 10, 2015

(87) PCT Pub. No.: WO2014/006234
PCT Pub. Date: Jan. 9, 2014

(65) Prior Publication Data
US 2015/0213299 A1    Jul. 30, 2015

(51) Int. Cl.
*G06K 9/00* (2006.01)
*G06T 7/00* (2017.01)
(Continued)

(52) U.S. Cl.
CPC ......... *G06K 9/0063* (2013.01); *G06K 9/4604* (2013.01); *G06K 9/4642* (2013.01);
(Continued)

(58) Field of Classification Search
CPC ....... G06T 7/0002; G06T 7/0008; G06T 7/11; G06T 2207/10016; G06T 2207/10032;
(Continued)

(56) References Cited

U.S. PATENT DOCUMENTS

| 3,783,284 A | 1/1974 | McCormack |
| 3,899,213 A | 8/1975 | Fantasia et al. |

(Continued)

FOREIGN PATENT DOCUMENTS

| CN | 101414009 A | 4/2009 |
| GB | 1543320 | 4/1979 |

(Continued)

OTHER PUBLICATIONS

Reed et al. "Oil spill modeling towards the close of the 20th century: overview of the state of the art." Spill Science & Technology Bulletin 5.1 (1999): 3-16.*

(Continued)

*Primary Examiner* — Katrina Fujita
(74) *Attorney, Agent, or Firm* — Squire Patton Boggs (US) LLP

(57) ABSTRACT

The invention relates to a method for detecting hydrocarbon spill in an aqueous medium from a plurality of images of the surface of the aqueous medium obtained by an infrared camera comprising analyzing an image of the plurality of images; checking whether at least one region that could be identified as spill is displayed in the image, in case of positive result, assessing whether the point representing a multidimensional vector of characteristics associated with the region is within a reference zone defined in a multidimensional space, this reference zone being representative of multidimensional vectors of characteristics of regions corresponding to real spills; if it is determined that the point representing the multidimensional vector of characteristics
(Continued)

is within the multidimensional reference zone, generating a warning signal of spill.

14 Claims, 7 Drawing Sheets

(51) Int. Cl.
| | | |
|---|---|---|
| G06K 9/46 | (2006.01) | |
| G06T 5/00 | (2006.01) | |
| H04N 5/33 | (2006.01) | |
| G06T 7/11 | (2017.01) | |
| G01N 33/18 | (2006.01) | |

(52) U.S. Cl.
CPC .............. *G06T 5/002* (2013.01); *G06T 5/009* (2013.01); *G06T 7/0002* (2013.01); *G06T 7/0008* (2013.01); *G06T 7/11* (2017.01); *H04N 5/33* (2013.01); *G01N 33/1826* (2013.01); *G06K 2009/00644* (2013.01); *G06T 2207/10016* (2013.01); *G06T 2207/10032* (2013.01); *G06T 2207/10048* (2013.01); *G06T 2207/20021* (2013.01); *G06T 2207/20076* (2013.01); *G06T 2207/30181* (2013.01)

(58) Field of Classification Search
CPC . G06T 2207/10048; G06T 2207/20021; G06T 2207/20076; G06T 2207/30181; G06T 5/002; G06T 5/009; G06K 9/0063; G06K 9/4604; G06K 9/4642; G06K 2009/00644; G01N 33/1826; H04N 5/33
See application file for complete search history.

(56) References Cited

U.S. PATENT DOCUMENTS

| | | | |
|---|---|---|---|
| 3,961,187 A | 6/1976 | Barringer | |
| 4,517,458 A | 5/1985 | Barringer | |
| 4,897,551 A | 1/1990 | Gersh et al. | |
| 4,933,678 A * | 6/1990 | Tennyson | G01S 13/88 342/176 |
| 5,296,711 A | 3/1994 | Leonard et al. | |
| 6,809,760 B1 * | 10/2004 | Takagi | G01S 3/781 348/143 |
| 7,391,442 B1 * | 6/2008 | Fleischman | G03B 17/06 348/222.1 |
| 8,917,175 B2 * | 12/2014 | O'Regan | G01S 5/0027 340/539.1 |
| 2003/0063006 A1 | 4/2003 | Gutta et al. | |
| 2008/0197284 A1 | 8/2008 | Ebenstein et al. | |
| 2009/0039255 A1 | 2/2009 | Andrews et al. | |
| 2011/0060551 A1 * | 3/2011 | Elhajj | G01B 7/06 702/166 |
| 2011/0181279 A1 * | 7/2011 | Srnka | G01N 24/08 324/307 |
| 2013/0147951 A1 * | 6/2013 | Brown | G01N 25/18 348/143 |

FOREIGN PATENT DOCUMENTS

| | | |
|---|---|---|
| WO | WO 2009/023552 A2 | 2/2009 |
| WO | WO 2010/128860 A1 | 11/2010 |
| WO | WO 2012/021753 A2 | 2/2012 |

OTHER PUBLICATIONS

Application Story—Flir Thermal Imaging Cameras Ideal for Oil Detection, URL: http://www.trueheading.se/files/document/products/flir/appstories/Flir%20app%20note%20-%20oil%20spill%20recovery.pdf, Jan. 13, 2011, 2 pp.

Brekke and Solberg "Oil Spill detection by satellite remote sensing," Remote Sensing of Environment, 2005, vol. 95, pp. 1-13.

Kontitsis et al. "A UAV Vision System for Airbone Surveillance," Proceedings of the 2004 IEEE International Conference on Robotics & Automation, Apr. 2004, pp. 77-83.

Leifer et al. "State of the art satellite and airborne marine oil spill remote sensing: Application to the BP *Deepwater Horizon* oil spill," Remote Sensing of Environment, 2012, vol. 124, pp. 185-200.

Srinivasan et al. "A survey of sensory data boundary estimation, covering and tracking techniques using collaborating sensors," Pervasive and Mobile Computing, 2012, vol. 8, pp. 358-375.

Yilmaz et al. "Target tracking in airborne fordward looking infrared imagery," Image and Vision Computing, 2003, vol. 21, pp. 623-635.

* cited by examiner

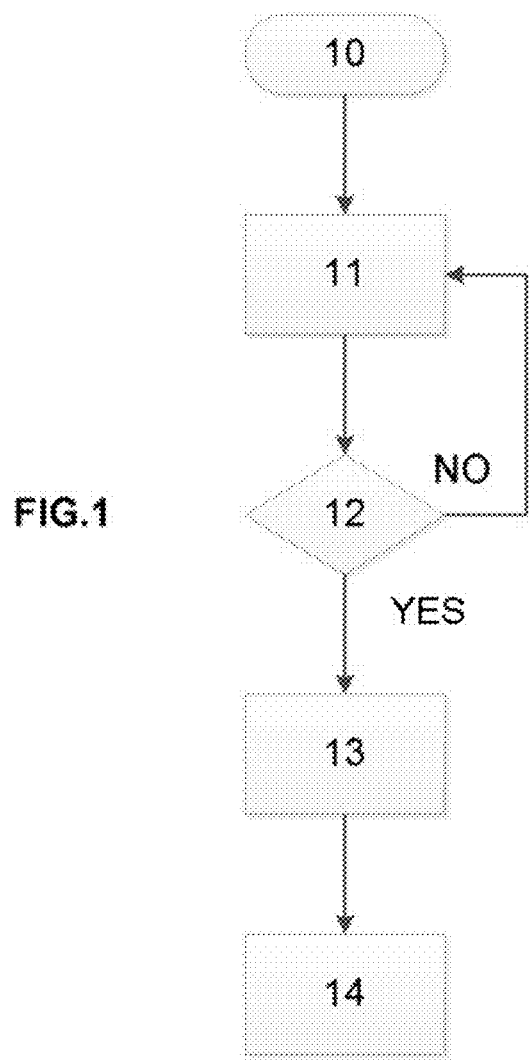
FIG.1
FIG.2
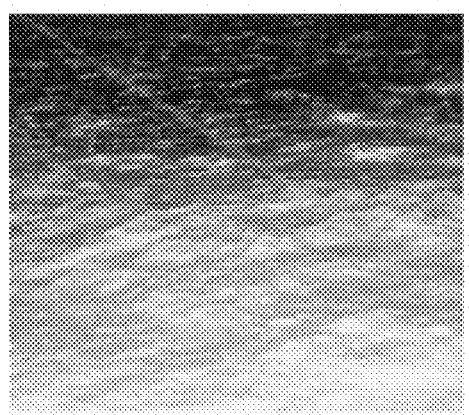
(a)
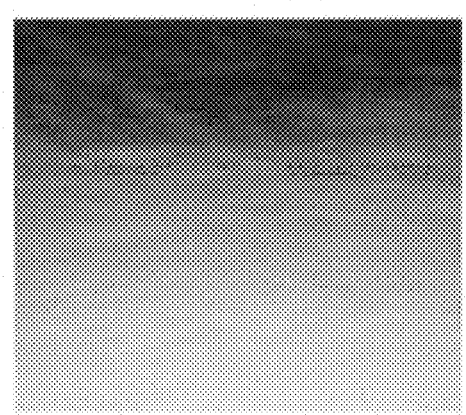
(b)

(a)

(b)

(a)

(b)

FIG.5
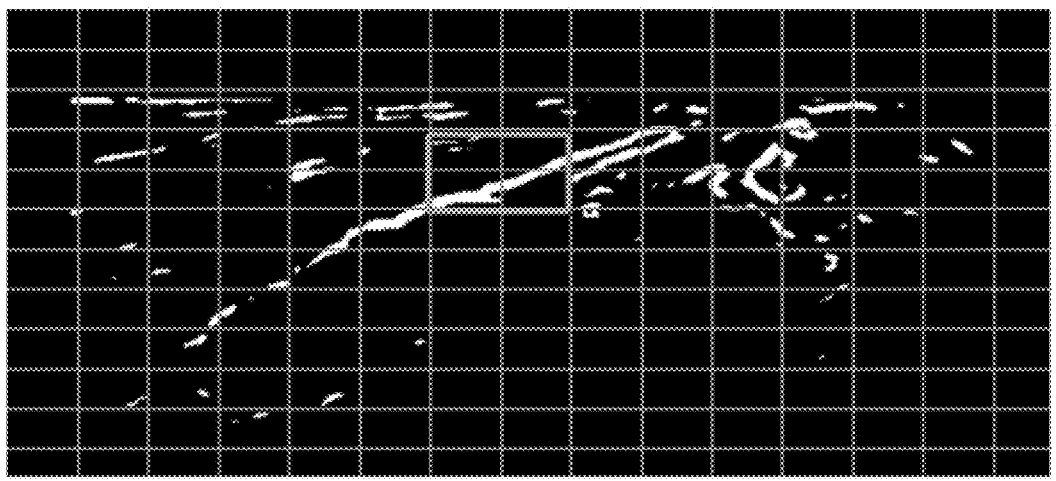
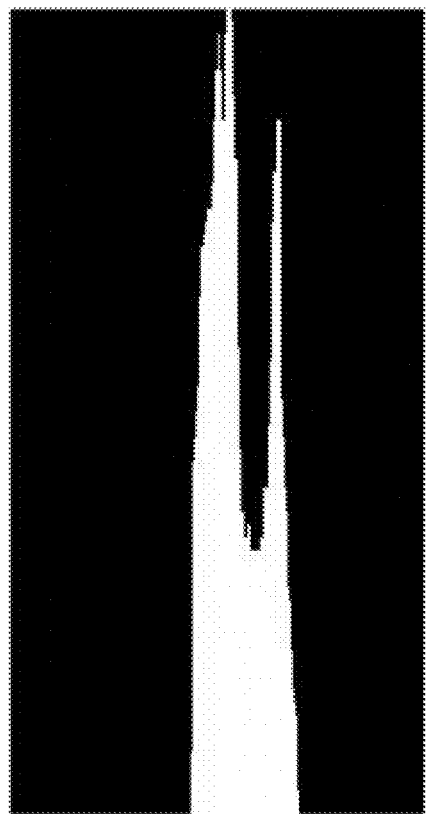
FIG.6

(a) (b) (c) (d)

(a) (b) (c) (d)

(a)  (b)

(c)  (d)

(a)  (b)

(c)  (d)

(a)

(b)

(c)

(d)

INFRARED IMAGE BASED EARLY DETECTION OF OIL SPILLS IN WATER

The present invention relates to a method for detecting hydrocarbon spill in an aqueous medium from a plurality of images of the surface of the aqueous medium obtained through an infrared camera. More specifically, the invention relates to a method for early detection of hydrocarbon spills on aqueous surfaces, such as sea surfaces, from images obtained through an infrared camera.

The invention further relates to an electronic system and a computer program suitable for carrying out this method.

The invention may be used and installed in fixed platforms, boats, refinery marshlands and commercial and industrial ports. It further has other fields of application such as monitoring of vessels, detection of persons and/or tracking and predicting of the path of discharges or spills in an aqueous medium.

STATE OF THE ART

Large accidental spills of hydrocarbons in general and oil in particular often have a great media impact and they usually raise the awareness of the public. Such spills tend to affect costs and they symbolize the problem of marine oil pollution. These spills, however, only represent between 10 and 15 percent of all the oil reaching seas/oceans every year.

A long list could be obtained of oil tankers, oil wells and deep sea pipelines which, over the years, have caused major and spectacular accidental oil spills in the marine environment. These spills have usually caused in the short and long term significant damages to coastal and marine habitats and ecosystems, seabirds, mammals, fishing and even people.

There may be other sources of marine pollution by oil or derivatives thereof that are not as spectacular, and therefore they may be not linked to marine oil pollution. For example, sea oil pollution may also be caused by rainwater and/or by already polluted municipalities' wastewater in many coastal facilities consuming oil and/or derivatives, by gaseous or liquid hydrocarbons from vehicles and/or powerboat(s), etc. While these other sources do not have a media impact as major accidental leaks, they are often a large and endless spill of oil and/or derivatives to the marine environment.

A large part of the oil polluting the seas/oceans comes from natural sources such as natural seepages in the seabed, in which case they can not be avoided. But the largest and most important source of oil reaching coastal and marine environments around the world is by far from land based sources as a result of ordinary, everyday activities of humans.

As quoted by way of example, the Deep Water Horizon accident in the Gulf of Mexico opened the debate on the issue of early spill detection on a global scale.

Thus, oil spill detection in the marine environment is now a key discipline for the preservation of seas and oceans and, more importantly, their early detection. Once spills are detected, different techniques for separating and subsequently removing them from the seawater may be applied.

Different types of devices for detection of spills of oil or derivatives in the sea are known in the art. Some of these devices are based on cameras for viewing portions of the sea so that oil spills are highlighted such that they can be detected with a given accuracy.

For example, document [Application Story—Flir Thermal Imaging Cameras Ideal for Oil Detection], which can be found in, for example, the following web link: http://www.flir.com/uploadedFiles/CS_EMEA/Application_Stories/Media/Downloads/Oilspill_EN.pdf, discloses infrared cameras based on remote generation of images from accurate temperature measurement without physical contact with the object to be studied (in this case, oil spills). Basically, these infrared cameras are capable of identifying hydrocarbon spills on the surface of an aqueous medium from thermal and emissive differences of substances that have been spilled or discharged relative to the surface of the aqueous medium.

Measuring of these temperatures is carried out by acquiring infrared radiation of the electromagnetic spectrum, and this radiated energy is converted into temperature information. Finally, some images representing a sort of maps of detected temperatures are obtained, in which water and oil can be distinguished due to the different thermal properties of both elements.

However, these cameras and possible systems associated therewith require constant and skilled monitoring and handling which often results in high operating costs and a certain risk of inaccuracy in the results of the overall spill detection process. Although these cameras provide for high quality resolution and/or accuracy, a poor operation thereof may also result in poor results.

SUMMARY OF THE INVENTION

It is an object of the present invention to provide a method for detecting hydrocarbon spill in an aqueous medium from a plurality of images of the surface of the aqueous medium obtained by an infrared camera, which avoids at least some of the above mentioned known prior art disadvantages.

According to one aspect of the invention this is achieved by a method for detecting hydrocarbon spill in an aqueous medium from a plurality of images of the surface of the aqueous medium obtained by an infrared camera, comprising:

Analysing one image of the plurality of images of the surface of the aqueous medium;

Checking whether at least one region that could be identified as hydrocarbon spill is displayed in the analysed image of the surface of the aqueous medium;

In case of positive result in checking,

Assessing whether the point representing a multidimensional vector of characteristics associated with the region that could be identified as an hydrocarbon spill is within a reference zone defined in a multidimensional space, this reference zone being representative of multidimensional vectors of characteristics of regions corresponding to actual hydrocarbon spills in an aqueous medium;

If it is determined that the point representing the multidimensional vector of characteristics associated with the region that could be identified as hydrocarbon spill is within the multidimensional reference area, generating a warning signal of hydrocarbon spill in the aqueous medium.

Thus, through the definition of a reference area in a multidimensional space and through the characterization (by a multidimensional vector of characteristics) of each of the regions that could be considered as spills, it is possible to automatically determine the presence of a spill in the sea (or any other aqueous or water medium), a spill alarm being generated without requiring the presence of an operator. For this purpose, it is necessary to check whether the point representing the multidimensional vector of characteristics associated with the region that could be considered as a spill is within the reference zone defined in the multidimensional space. If this is the case, the system implementing the method is capable by itself of generating the warning signal.

To obtain this multidimensional vector of characteristics it is necessary to perform the analysis of an image (or frame) from the surface of the aqueous medium obtained by an infrared camera. More specifically, a video sequence of the surface of the aqueous medium can be acquired or captured by the infrared camera which is subsequently converted into a plurality of images or frames.

While the above method is executed by the system, a new video sequence can be captured in parallel by the infrared camera, which will be analysed upon analysing the previously obtained video sequence. Of course if during an image analysis at least one region that could be identified as hydrocarbon spill is not detected, the system proceeds to analyse the next image in the plurality of images, that is, the method control returns to the image analysis step.

Preferably, analysing an image in the plurality of images of the surface of the aqueous medium may comprise:
  Segmenting the image of the surface of the aqueous medium in order to split the image into regions;
  Obtaining a multidimensional vector of characteristics representative of the static region that could be identified as hydrocarbon spill.

Segmenting the image under analysis allows obtaining a binary image in black with found regions in white. Thus, the binary image of each detected region serves as a mask for the analysis of characteristics of the region, which facilitates the step of obtaining a multidimensional vector of characteristics of each detected regions.

Moreover, analysing an image of the plurality of images of the surface of the aqueous medium may further comprise:
  Conditioning the image of the surface of the aqueous medium;
and wherein segmenting the image of the surface of the aqueous medium may comprise:
  Segmenting the conditioned image.

Prior to the segmentation step it is possible to carry out an image pre-processing or pre-conditioning which has the purpose of enhancing results obtained in the segmentation step. For example, the image pre-processing may thus comprise:
  Reducing noise in the image of the surface of the aqueous medium;
  Correcting variations in the image intensity due to differences in the angle of the infrared camera relative to the surface of the aqueous medium.

Image noise reduction may be regarded as the removal of ripple in the sea or aqueous medium, the ripple in the sea being considered as noise and the possible regions that may be identified as spill, being considered as relevant information.

On the other hand, the distance darkening correction is intended to correct or compensate for the darkening effect that occurs in the image due to differences in the angle of the infrared camera relative to the surface of the aqueous medium, resulting in the camera receiving different emissivity from the surface of the aqueous medium as a result of such angle differences, thus obtaining a more uniform image in terms of grey levels, with no loss of relevant information.

In addition, conditioning of the image of the surface of the aqueous medium may further comprise:
  Identifying the aqueous medium in the image.

This step of the method is suitable so that further processing performed on the image under analysis is carried out only on the relevant area of the image, which is the aqueous medium, helping in achieving the goal of spill detection. In this way, possible misunderstandings during image processing (e.g., errors due to misidentified objects within the image) can be avoided and even a reduction of processing requirements of the system implementing the procedure may occur.

According to one embodiment of the invention, the multidimensional vector of characteristics associated with the region that could be identified as hydrocarbon spill may be the multidimensional vector of characteristics representative of the static region that could be identified as hydrocarbon spill.

Once the image analysis has been performed, which includes obtaining the multidimensional vector of characteristics representative of the static region that could be identified as hydrocarbon spill, it is checked whether any region that could be identified as spill exists in the image. In case of a positive result in this checking, it is possible to determine whether the region really corresponds to a spill, assessing whether the multidimensional vector of characteristics representative of the region is in the reference area set within the multidimensional space. As stated above, in case of a negative result in checking, the process control returns to the analysis step, since the analysed image does not provide information for spill detection.

By "multidimensional vector of characteristics representative of the static region" is meant a vector of characteristics representative of a region detected within a static image or frame, that is, the temporal evolution of the region in different frames is not taken into account.

According to a further embodiment of the invention, in case of a positive result in the checking of whether at least one region that could be identified as hydrocarbon spill is displayed in the analysed image of the surface of the aqueous medium, the method may comprise:
  Checking whether the region has been previously entered into a data repository relating to areas that could be identified as hydrocarbon spill in the aqueous medium, the repository comprising an identifier of each region and a multidimensional vector of characteristics for each image analysed region;
  In case of a negative result in checking
    entering an identifier of the region and the multidimensional vector of characteristics obtained from the region into the data repository, for the analysed image;
  In case of positive result in checking,
    entering the multidimensional vector of characteristics obtained from the region for the analysed image into the data repository associated with the identifier of the region;
    generating a multidimensional vector of characteristics representative of the dynamics of the region, from the multidimensional vector of characteristics associated with the identifier of the region;
and wherein the multidimensional vector of characteristics associated with the region that could be identified as hydrocarbon spill is the multidimensional vector of characteristics representative of the dynamics of the region generated.

In the event that the temporal evolution of the region along different frames (or images) is desired to be taken into consideration in order to determine if this is a spill, the described steps can be performed. It is thus possible to use a data repository for storing the multidimensional vector of characteristics representative of the static region, for each image under examination, so that a plurality of these vectors are finally provided from which it is possible to obtain a multidimensional vector of characteristics representative of the dynamics of the region, that is, it is possible to obtain a vector of characteristics in which the temporal evolution of the region is represented through the different analysed images.

Alternatively, it is possible to obtain the multidimensional vector of characteristics representative of the dynamics of the region from the processing of each of the multidimensional vector of characteristics representative of the static region, as is obtained by the system. Thus, for example, for the first multidimensional vector of characteristics representative of the static region obtained (that is, the vector representative of the region for an image), the multidimensional vector of characteristics representative of the dynamics of the region will be identical to the first vector. When a second multidimensional vector of characteristics representative of the static region (that is, the vector of characteristics representative of the same region but for another image under analysis) is obtained by the system, the multidimensional vector of characteristics representative of the dynamics of the region will be different since it already contains information from both the first vector obtained and the second. In this way, the use of a data repository is avoided since the multidimensional vector of characteristics representative of the dynamics of the region is being obtained in real time.

At this point it is important to note that the dynamic characteristics supplement but not replace the static characteristics. If the static characteristics are initially collected on a vector $V=[v1, v2, v3, \ldots vN]$ and from this vector the dynamic characteristics, which are collected on a vector $W=[w1, w2, w3, \ldots, wM]$, are calculated, the new vector of characteristics, having a static part and a dynamic part, is formed by $X=[v1, v2, v3, \ldots, vN, w1, w2, w3, \ldots, wM]$. This new vector X is the one used for the generation of the alarm of spill.

According to a second aspect the invention a computer program is provided comprising program instructions for causing a computer system to execute the method for detecting hydrocarbon spill in an aqueous medium from a plurality of images of the surface of the aqueous medium obtained by an infrared camera, described above.

This computer program may be stored on physical storage media such as recording media, a computer memory, or a read only memory, or it may be carried by a carrier wave, such as electrical or optical.

According to a third aspect of the invention there is provided an electronic system for detecting hydrocarbon spill in an aqueous medium from a plurality of images of the surface of the aqueous medium obtained by an infrared camera, comprising:
  Electronic means for analysing an image of the plurality of images of the surface of the aqueous medium;
  Electronic means for checking whether at least one region that could be identified as hydrocarbon spill analysed is displayed in the image of the surface of the aqueous medium;
  In case of positive result in checking,
  Electronic means for providing a multidimensional vector of characteristics associated with the region that could be identified as hydrocarbon spill;
  Electronic means for assessing whether the point representing the multidimensional vector of characteristics associated with the region that could be identified as hydrocarbon spill is within a reference zone defined in a multidimensional space, this reference zone being representative of multidimensional vectors of characteristics in regions corresponding to actual hydrocarbon spills in an aqueous medium;
  Electronic means for generating a warning signal of hydrocarbon spill in the aqueous medium, if it is determined that the point representing the multidimensional vector of characteristics associated with the region that could be identified as hydrocarbon spill is within the multidimensional reference area.

Therefore, it is possible to execute the described method both from a computer program and from an electronic system, such as a FPGA, ASIC, or a programmable logic controller.

According to further aspect the invention provides a computer system for detecting hydrocarbon spill in an aqueous medium, comprising:
  An infrared camera adapted for obtaining a plurality of images of the surface of the aqueous medium;
  A memory and a processor containing instructions stored in the memory and executable by the processor, the instructions comprising functionality for:
    Analysing one image of the plurality of images of the surface of the aqueous medium obtained by the infrared camera;
    Checking whether at least one region that could be identified as hydrocarbon spill is displayed in the analysed image in the surface of the aqueous medium;
    in case of positive result in checking,
      Providing a multidimensional vector of characteristics associated with the region that could be identified as hydrocarbon spill;
      Assessing whether the point representing the multidimensional vector of characteristics associated with the region that could be identified as hydrocarbon spill is within a reference zone defined in a multidimensional space, this reference zone being representative of multidimensional vectors of characteristics of regions corresponding to actual hydrocarbon spills in an aqueous medium;
      If it is determined that the point representing the multidimensional vector of characteristics associated with the region that could be identified as hydrocarbon spill is within the reference area multidimensional, generating a warning signal of hydrocarbon spill in the aqueous medium.

The invention further provides a method for detecting hydrocarbon spill on the surface of an aqueous medium, comprising:
  Receiving a warning signal of detection of hydrocarbon spill in the aqueous medium generated from at least one image obtained by a radar;
  Checking whether there is an infrared camera capable of monitoring the spill;
  In case of negative result,
    Generating a warning signal of detection of hydrocarbon spill in the aqueous medium from the warning signal of detection generated from the at least one image obtained by a radar;
  In case of positive result,
    Executing the method for detecting hydrocarbon spill in an aqueous medium from a plurality of images of the surface of the aqueous medium obtained by an infrared camera, as described above.

Thus, a method for detecting a spill can be executed involving data provided by two sensors based on different physical principles, that is, a radar and an infrared camera, which provides a number of advantages, such as greater operability (more operating hours per year) and lower probability of false alarms. Basically, the advantage of the radar that allows large areas to be covered within a short time (although it has a high false alarm rate) is combined with the advantages of the infrared camera, the most glaring of which is the fact that it has a good coverage area (although not as large as that of the radar), allows detection in the shadow zone of the radar (this feature being especially important in fixed installations), and since they are passive elements, they do not pose any security risk to human beings or the environment.

Depending on weather conditions, the radar can act as a primary sensor, constantly monitoring the area of interest of the surface of the aqueous medium and capturing video sequences which are subsequently analysed through an algorithm for interpretation of these images. The output of this interpretation algorithm indicates whether there is a possible spill or not and, in case of spill, it can also provide information on the spill, such as its geographic position (geo-location) or the extent of the spill.

In the event that the algorithm output result corresponds to the absence of spill, the next image obtained by radar is processed by this interpretation algorithm.

In the event that the result of the output of this algorithm corresponds to a possible spill, this output feeds the input of the system that executes the method for detecting hydrocarbon spill in an aqueous medium from a plurality of images of the surface of the aqueous medium obtained by an infrared camera, described above. The infrared camera acts as a secondary sensor so that when an indication of a possible spill from the radar interpretation algorithm is received, a video sequence of the area of interest of the surface of the aqueous medium is captured for further processing, as described above.

On the other hand, if weather conditions do not allow the conditions of the surface of the aqueous medium to be detected by the radar, the infrared camera acts as a single automatic monitoring sensor. In this case, all of the above is applicable to the infrared camera when running standalone.

According to one embodiment of the invention, in case of positive result in checking whether there is an infrared camera suitable for monitoring the spill, the method may comprise:
Positioning the infrared camera.
The method may further comprise:
Receiving the geographical position of hydrocarbon spill in the aqueous medium;
and wherein checking whether there is an infrared camera capable of monitoring the spill comprises checking whether there is an infrared camera capable of monitoring the surface of the aqueous medium that is in the received geographical position.

Furthermore, the invention further provides a computer program comprising program instructions for causing a computer system to execute the method for detecting hydrocarbon spill in an aqueous medium, as described above.

This computer program may be stored on physical storage media such as a recording media, a computer memory, or a read only memory, or it may be carried by a carrier wave, such as electrical or optical.

Furthermore, the invention provides an electronic system for detecting hydrocarbon spill on the surface of an aqueous medium, comprising:
Electronic means for receiving a warning signal of detection of hydrocarbon spill in the aqueous medium from the warning signal of detection generated from at least one image obtained by a radar;
Electronic means for checking whether there is an infrared camera capable of monitoring the spill;
In case of negative result,
Electronic means for generating a warning signal of detection of hydrocarbon spill in the aqueous medium from the warning signal of detection generated from the at least one image obtained by a radar;
In case of positive result,
Electronic means for executing the method for detecting hydrocarbon spill in an aqueous medium from a plurality of images of the surface of the aqueous medium obtained by an infrared camera, as described above.

Finally, the invention provides a computer system for detecting hydrocarbon spill in the surface of an aqueous medium, comprising:
At least one radar;
At least one infrared camera;
A memory and a processor containing instructions stored in the memory and executable by the processor, the instructions comprising functionality for:
Receiving a warning signal of detection of hydrocarbon spill in the aqueous medium generated from at least one image obtained by the radar;
Checking whether there is an infrared camera capable of monitoring the spill;
In case of negative result,
Generating a warning signal of detection of hydrocarbon spill in the aqueous medium from the warning signal of detection generated from the at least one image obtained by a radar;
In case of positive result,
Executing the method for detecting hydrocarbon spill in an aqueous medium from a plurality of images of the surface of the aqueous medium obtained by an infrared camera, as described above.

Further objects, advantages and features of embodiments of the invention will become apparent to those skilled in the art from the description or may be learned by practice of the invention.

BRIEF DESCRIPTION OF THE DRAWINGS

Particular embodiments of the present invention will be now described by way of a non-limiting example, with reference to the accompanying drawings in which:

FIG. 1 shows a flowchart representative of the method for detecting hydrocarbon spill in an aqueous medium from a plurality of images of the surface of the aqueous medium obtained by an infrared camera according to one embodiment of the present invention;

FIG. 2 shows the result of applying a function for removing the ripple of the sea on a first image (a), which represents the snapshot (or frame) of the sea, wherein an image (b) representing the image average is obtained;

FIG. 5 shows a diagram of a gradient image with a selected cell during image segmentation step;

FIG. 6 shows a histogram chart calculated for the cell selected in FIG. 5;

DETAILED DESCRIPTION OF EMBODIMENTS

Figure 3:
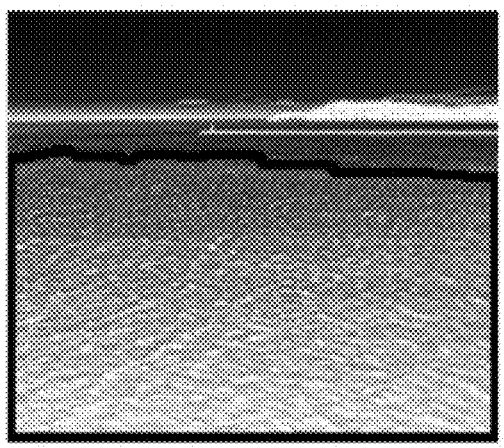
FIG. 3 shows different examples (a) and (b) of detection of areas of interest (ROI) within the images obtained by the infrared camera.
Figure 3:
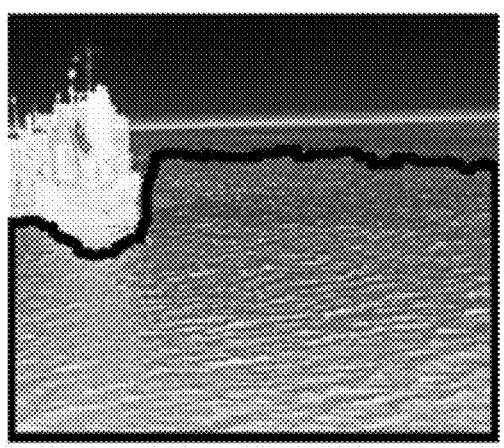

Preferred embodiments of the invention will be described below in which the aqueous medium is the sea. In addition, preferred embodiments of the method according to the invention will be described, which can be implemented from an electronic system, such as a FPGA, comprising all the electronic means necessary for executing the method according to the invention.

Alternatively, the method may be also implemented from a computer program, or a plurality thereof, running on a suitable information system, such as a desktop computer.

As shown in FIG. 1, starting from an initial situation 10 in which the method is caused to start, a preferred embodiment of the method for detecting hydrocarbon spill in the sea from a plurality of images of the surface of the sea obtained by an infrared camera, according to the invention basically comprises:

Analysing 11 one image of the plurality of images of the surface of the sea;

Checking 12 whether at least one region that could be identified as hydrocarbon spill is displayed in the analysed image of the surface of the sea;

in case of positive result in checking,

Assessing 13 whether the point representing a multidimensional vector of characteristics associated with the region that could be identified as hydrocarbon spill is within a reference zone defined in a multidimensional space, this reference zone being representative of vectors of multidimensional characteristics of regions corresponding to actual hydrocarbon spills in the sea;

If it is determined that the point representing the multidimensional vector of characteristics associated with the region that could be identified as hydrocarbon spill is within the multidimensional reference area, generating 14 a warning signal of hydrocarbon spill in the aqueous medium At this point it is important to note that the plurality of images of the surface of the aqueous medium can be obtained from a video file generated by the infrared camera, so that the plurality of images corresponds to a plurality of frames of the video file.

Alternatively, a real time video signal from the infrared camera may be received by the system so that the video signal may be analysed frame by frame by the system in order to detect a spill. Therefore, in this case, no video file would be generated by the infrared camera.

On the other hand, it is also important to note that the method can be executed several times until the presence of a region that could be identified as hydrocarbon spill is determined in one of the images of the plurality of images obtained by the infrared camera. Therefore, if the result of the described checking is negative, that is, at least one region that could be identified as hydrocarbon spill is not displayed in the analysed image of the surface of the aqueous medium, the method will be restarted with the following or another image of the plurality of images captured by the infrared camera being analysed.

Similarly, if more than one region that could be identified as hydrocarbon spill is displayed it has to be assessed whether the point representing the multidimensional vector of characteristics associated with each region that could be identified as hydrocarbon spill is within the reference area defined in the multidimensional space described above. In case that it is determined that a region corresponds to a spill, an alarm can be generated directly, or the method can still be executed until assessment of each of the vectors of characteristics is completed to determine the relevance of the spill, and subsequently generating an alarm of spill. With this latter configuration more information about the spill can be obtained (e.g., geographical position, extent or shape), all this information being provided together with the alarm of spill.

As described, the method comprises a first step of analysing the image of the surface of the sea which, in turn, comprises:

Performing an image pre-processing;

Performing a segmentation of the pre-processed image, and

Performing an extraction of the vector of characteristics of each segmented region of the image.

Performing the pre-processing of the image under analysis (more specifically, conditioning of the image) is suitable to promote or facilitate subsequent segmentation.

In order to perform such pre-processing or conditioning of the image it is desirable to mainly execute three functions:

Removing ripple of the sea shown in the image;

Providing the region of interest (hereinafter referred to as ROI) on which the rest of the processing is to be performed. Basically, it is a matter of detecting the sea or the aqueous medium within the image or frame under analysis, and Correcting the variation on image intensity due to differences in the angle of the infrared camera relative to the surface of the sea.

For executing the first function, that is, for removing ripple of the aqueous medium as shown in the image, an averaging of obtained frames is performed. For this purpose, sea ripple is considered as noise and possible hydrocarbon spills as relevant information. Therefore, by performing the frame averaging signal to noise ratio is improved as shown in FIG. 2. Clearly, between the image (a), representing the snapshot (or frame) of the aqueous medium (i.e., the frame obtained from the video file generated by the infrared camera), and the image (b) in FIG. 2, representing the image averaging, a removal of the ripple of the aqueous medium occurs.

Such frame averaging is performed on a number of frames "n" with said number "n" being configurable. The more frames are averaged, the greater is the removal of the ripple of the sea. The resulting image is obtained for each pixel by:
 Adding the grey level of that pixel into each frame, and
 Dividing the resulting value by the value of integrated frames "n".

That is, this could be expressed mathematically as follows:

$$(p(x,y)|n=0 + p(x,y)|n=1 + p(x,y)|n=2 + \ldots p(x,y)|n=m-1)/m = p(x,y)$$

of the averaged image, wherein:
 x: the horizontal coordinate;
 y: the vertical coordinate;
 n: the frame number (1st, 2nd, 3rd . . . );
 m: the number of frames, and
 p(x, y): a point within the frame.

With regard to the second function within pre-processing with regard to the provision of the ROI on which the rest of the processing is to be performed, according to a preferred embodiment of the invention, "n" input frames are taken and pixel grey values during the "n" frames are stored and a discrete cosine transform (DCT) is performed on these values. It should be noted that such ROI detection is performed on the averaged image obtained from application of the above described first function. The grid representing the pixel belongs to the ROI if the spectral power of this pixel level of grey is above a set threshold.

Examples of ROI detection can be seen in FIG. 3. Thus, the image (a) of this figure shows how the described second function applied is capable of selecting virtually the entire surface of the sea, while the image (b) of the figure shows how the function is also capable of selecting virtually the entire surface of the sea, avoiding the figure of the boat in the image. ROI detection is represented by a thick black line.

Finally, with respect to the darkening distance correction (i.e., the correction of the image intensity variation), corresponding to the third function of the image pre-processing within the analysis thereof, according to a preferred embodiment of the invention, a correction suitable for obtaining a more uniform image in terms of grey levels with no loss of relevant information is applied.

Figure 4:
FIG. 4 shows the result of applying a correction factor on the first image (a), which corresponds to image (b) in FIG. 2, for obtaining the image (b), where the darkening effect in the area of the sea surface farthest from the camera is reduced due to differences in the angle of the infrared camera relative to the sea surface.
Figure 4:
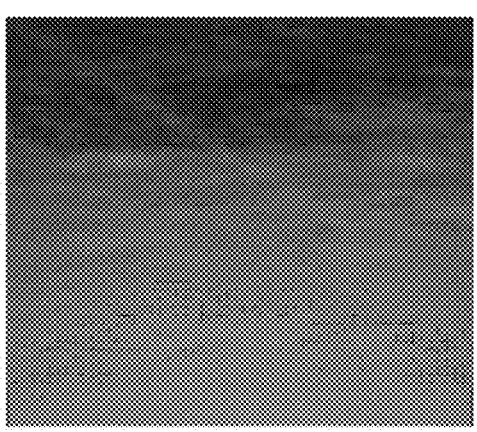

More specifically, as shown in FIG. 4, in the image (a), which corresponds to the image (b) in FIG. 2 with the detected ROI, i.e. it is the image averaged during the step of removing the ripple of the sea shown in the image and on which at least one ROI has been detected, a darkening effect at the upper part thereof corresponding to the area of the surface of the sea farthest from the camera is produced. This is due to differences in the angle of the infrared camera relative to the sea surface, which makes the emissivity captured by the infrared camera to be different. With the purpose of obtaining the image (b) in FIG. 4, a correction factor is applied that is calculated from the study of the averaged image represented by the image (a) of this figure. More specifically, the image is divided into columns, within each of which the first derivative of the grey level in the vertical direction is calculated and the correction factor is obtained for that column. With the resulting values of each column an overall correction factor is generated that corrects this effect.

Once the image pre-processing has been performed and following the image analysis a segmentation of the resulting image is performed with the purpose of separating the objects in the background image.

For this purpose, the pre-processed image and the ROI are taken as an input and a binary image in black, with the found objects in white, is generated as an output.

The segmentation of the resulting image involves the following steps:
 Mean-shift segmentation: it allows an iterative search for clusters in the image corresponding to local maximum values of estimated probability density distribution by a kernel K. Those pixels in spatial proximity whose gradient is below a threshold are grouped by the algorithm, with the various image components being thus separated.
 Study the mean-shift segmentation image: the gradient operator is applied to the image obtained by the mean-shift segmentation and this is studied locally by dividing the image into cells and calculating the number of white pixels in each one of them. This number of white pixels represents the level of sea temperature change: the higher the temperature change, the more the white pixels. If this number exceeds a threshold value, the selected cell is marked as being useful for subsequent thresholding. Cell selection on the image gradient is shown in FIG. 5.
 Turning to the Mean-Shift segmentation image, the histogram is calculated in the same cells marked in the previous step, obtaining a histogram in each cell with a bimodal distribution, such as that shown in FIG. 6. This histogram distribution allows two distinct classes within that cell to be separated. The grey level used for thresholding is the grey level of the overall minimum of the histogram.
 Finally, a global thresholding of the image obtained from the mean-Shift segmentation is performed. With all the overall minimum obtained, the overall threshold is calculated with which the final thresholding is performed yielding a binary image with the segmented regions differing from the background, and which may correspond to possible spills. The binary image of each detected region serves as a mask for the analysis of characteristics of the region.

Once the binary image obtained with the segmented regions, and according to a preferred embodiment of the invention, certain characteristics from each of the segmented regions are extracted. With the characteristics obtained for each region a multidimensional vector of characteristics associated therewith is generated or obtained.

For extracting characteristics of each region the "cvBlobsLib" library from OpenCV suitable for extracting Blobs (Binary Large Objects) can be used, so that the connected components of the image are provided. In order to find the connected components, the algorithm checks the connectivity between pixels, which are connected if they can find a way for which the values of the pixels have the same value along the way. Basically the binary image obtained above (an image only with two colours, white/black) is passed to blobs as the input, and white (or black) pixels and whose binding way may be made without going through a black (or white) pixel are grouped, giving an object list defined primarily by their geometrical characteristics as the output. Therefore, each group of white (or black) pixels takes a given shape involving an area, a perimeter, a spatial moment, and so on. In summary, the received binary image is "interpreted" by the Blobs as the input and the shapes they find are output.

From these obtained shapes of the different regions shown in the binary image it is possible to obtain certain characteristics that form the multidimensional vector of characteristics thereof, these vectors allowing a correct classification of the regions they represent to be performed.

According to a further embodiment of the invention, with the purpose of reducing processing time and releasing processing resources, prior to obtaining all necessary characteristics to generate the vector of characteristics of each region, it is possible to obtain only a part of these characteristics (e.g., size and geometry of each region), to perform a first classification of regions. Thus, those isolated and small regions are removed (i.e., based on their size) as well as those regions defined by straight lines or containing elements with straight sections of sufficient size (i.e., based on geometry) such that it will be only necessary to obtain the vector of characteristics of those regions having passed this first classification.

The multidimensional vector of characteristics representative of each region can be formed by the following morphological and texture metrics:

1. Perimeter;
2. Average of grey levels of blob pixels;
3. Standard deviation of grey levels of blob pixels;
4. Spatial moments;
5. Central moments;
6. Invariant moments;
7. Texture features: Entropy, contrast, homogeneity, correlation, energy.

In one a preferred embodiment of the invention, each vector of characteristics comprises 8 parameters representative of the region, which are obtained from the different morphological and texture metrics of the above described region (it is therefore a 8-dimension vector of characteristics). These parameters are as follows:

Perimeter;
x coordinate of the mass centre;
y coordinate of the mass centre;
Surface;
Entropy (texture);
Contrast (texture);
Homogeneity (texture);
Correlation (texture).

Clearly, the number of parameters to be considered for the vector of characteristics may vary from application to application. As a general rule, it will be necessary to take into account all those parameters characterizing correctly and sufficiently the regions.

Therefore, for each region identified in the binary image this octodimensional vector of characteristics is obtained, which allows the classification of each of the regions to be subsequently performed, discarding those detected regions which due to their characteristics are unlikely to correspond to a spill. This vector of characteristics is defined as a multidimensional vector of characteristics representative of the static region that could be identified as spill, i.e. it is a vector of characteristics associated with a particular region and image (or frame).

Three characteristics used to filter the regions are contemplated:

1. Size. Small and isolated regions are removed.
2. Geometry. Those regions defined by straight lines or containing elements with straight sections of sufficient size are removed.
3. Texture. Texture is a measure of properties such as roughness, homogeneity and regularity and it is used within this context to filter out those elements that do not correspond to known statistics of the spot, such as different types of objects, algae. The algorithm used for texture analysis is the grey level co-occurrence matrix (GLCM) in which second-order statistics of the GLCM matrix is measured in order to extract various parameters relating to texture:

Correlation: it measures the similarity between neighbouring pixels. It takes values ranging from 1 (identical neighbouring pixels) to −1 (different neighbouring pixels).
    Contrast: also referred to as "sum of the square variances". It provides a measure of how much the differences of grey levels vary.
    Entropy: it is a measure of uniformity of the histogram, the closer to uniform distribution (i.e. a more random texture) the higher the entropy. Conversely, the softer the texture (less random) the lower the entropy.
    Homogeneity: also referred to as "inverse difference moment". As the term suggests, it is related to texture homogeneity. This measure becomes large when contrast has a low value.
    Energy: also known as "uniformity". It provides the sum of the squares of the GLCM matrix elements.

Taking these characteristics into account a preliminary static classification can be performed, in which distinction is made between spots (that is, spills) and image background, and based on a discrimination function spots having a texture similar to the background image are discarded.

Obviously, if the above described first classification has been performed, this second classification will only be based on the texture of the region, since the size and geometry have been already assessed during the first classification. It is assumed that regions reaching this second classification meet size and geometry established requirements.

In case that the image comprises a region that could be identified as hydrocarbon spill (i.e., meeting size, geometry and texture established requirements), it is possible to use its octodimensional vector of characteristics (note that the multidimensional vector of characteristics and the number of dimensions depend on the parameters of the region contemplated in the vector) for determining whether the region is indeed a spill and thus generating an alarm of spill.

Thus following the above established method shown in FIG. 1, if the image under analysis comprises a given region that could be identified as hydrocarbon spill, it must be assessed whether the point representing the multidimensional vector of characteristics associated with the region that could be identified as hydrocarbon spill (i.e., the octodimensional vector of characteristics representative of the static region that could be identified as spill) is located within a reference zone defined in a octodimensional space, said reference zone being representative of octodimensional vectors of characteristics of regions corresponding to actual hydrocarbon spills in the sea.

If it is determined that the point representing the octodimensional vector of characteristics associated with the region that could be identified as spill is within the multidimensional reference area, a warning signal of hydrocarbon spill in the sea is generated.

Obviously, before performing the above mentioned assessment, it is essential to obtain the reference zone defined in the octodimensional space. For this purpose, images obtained by an infrared camera showing actual hydrocarbon spills in the sea are analysed, and vectors of characteristics are obtained for regions that meet size and geometry established requirements. Each of these vectors of characteristics obtained is a point in the octodimensional space, so that a cloud of these points yields the reference zone.

In the case that the point representing the vector of characteristics of a region that could be identified as spill is within the reference zone established in the octodimensional space, the electronic system implementing the method interprets that the region corresponds to an actual spill and it generates a warning signal indicative of the occurrence of spill.

According to one embodiment, the above described assessment on whether the point representing the octodimensional vector of characteristics associated with the static region that could be identified as a spill is within the multidimensional reference area may be ignored and tracking of the evolution over time of the spill can be performed from which an alarm of a spill is generated or not.

In this tracking step, time consistency is assigned to instantaneous detections in the previous step.

The input data of the tracking step have the following characteristics:
  There is a variable number of objects that can not be distinguished from each other only with their instantaneous characteristics. These objects:
    Appear at random positions in the space and at random times.
    Are characterized by continuously evolving parameters (e.g. continuous movement, in case of position).
    Persist for a random time and eventually disappear.
  Object detections occur at random time intervals.
  The measurements are noisy, such that:
    The probability of detection is <100%.
    False alarms occur.

The purpose of tracking is to relate each detection with a target persistent over time. Thus, the target is built on detections, which are integrated causing a behaviour compatible with the actual physical dynamics.

The tracking system maintains a database with targets present in the system. All the targets are in this database, regardless of whether they are classified as spills or not, as this is a subsequent process.

Two sub-processes are required for tracking:
Data association;
State estimation.

Data association consists in allocating frame detections with database targets. In case this association is not possible, a new tentative target will be then created.

There are different methods for data association: NN (Nearest Neighbour), MHT (Multiple Hypothesis Tracker), JPDAF (Joint Probabilistic Data Association Filter, etc.).

Data association is a mathematical problem of the NP-hard (non-deterministic polynomial-time hard) type, which means that its resolution is costly in time.

According to one preferred embodiment, the NN method is used since:
  It is easier to implement.
  It does not require to know in detail statistical distributions of noise (the JPDAF does).
  The MHT method is far more complex and it offers better time consistency. However, this application does not need this time consistency (understood as target identification) but obtaining the ability of classifying between detecting spill/no spill and NN is enough for this.

However, any other data association method could be used, for example any of those described above.

The NN implementation for this system comprises the following processes:
  Creating an array of detection-target distances:
    A windowing process is first used for removing unlikely associations;
    Mahalanobis distance is calculated between detection and all targets within the window.
  Selecting the best association:
    Due to the characteristic of being a NP-hard problem, a heuristic method is used for reaching a suboptimal solution in a short time. This suboptimal solution is based on giving priority to the association of largest detections, as they are considered less sensitive to noise effects.

On the other hand, state estimation consists in removing/reducing noise from detection measurements on the video sequence.

State estimation is typically performed with a Kalman filter, although it is possible to use other tools for performing this estimation. The basic Kalman filter assumes a physical model of linear dynamic behaviour and Gaussian distributions of noise.

The main constraints of the Kalman filter are generally due to the fact that the real physical system does not behave exactly as the model:
  Nonlinear dynamics;
  Non Gaussian noise.

There are variations of the Kalman filter that can be used in non-linearity situations, but they have disadvantages such as an increased complexity and occurrence of instabilities. Therefore, a standard Kalman filter is used in this system.

The dynamic classification is the process that decides whether a target detected in the video sequence is a spill or not. To do this, the temporal evolution of the characteristic parameters of the targets is observed, that is, an octodimensional vector of characteristics representative of the dynamics of region is obtained based on octodimensional vectors of characteristics representative of the static region that could be identified as spill.

According to one embodiment of the invention the rate of change of the parameters is only considered: growth rate (increase in area/perimeter), travel speed, rate of change of texture . . . . This speed estimation is performed as a part of the state estimation, within the tracking module.

In order to characterize the evolution of spills over time training videos are used from which typical rates of change are extracted. For this purpose, the data analysis and recording infrastructure which was already developed is used to adjust the above processes.

More specifically, it is assessed whether the point representing the octodimensional vector of characteristics representative of the dynamics in each region that could be identified as spill is located within a reference zone represented in the octodimensional space, although in this case the reference area is obtained from typical rates of change determined from training videos, as stated above.

The result of the classification is that only spills are marked as alarms and not other objects in the scene, i.e., a warning alarm signal of spill is generated if the octodimensional vector of characteristics representative of the dynamics of one of the regions is within the reference zone of the octodimensional space.

At this point it is important to note that the octodimensional vector of characteristics representative of the dynamics of each region can be obtained in different ways.

Thus, this vector can be obtained by using a data repository (e.g. a database) and the method steps are as follows:

Checking whether the region has been previously entered into the database relating to areas that could be identified as spill, the database comprising an identifier of each region and at least one octodimensional vector of characteristics of the region for each image (or frame) analysed;

In case of negative result in checking
Entering into the database an identifier of the region and the static octodimensional vector of characteristics obtained from the region, for the analysed image;

In case of positive result in checking,
Entering into the database, associated with the identifier of the region, the static octodimensional vector of characteristics obtained from the region, for the analysed image;
Generating the octodimensional vector of characteristics representative of the dynamics of the region from the static octodimensional vector of characteristics associated with the identifier of the region.

Alternatively, the octodimensional vector of characteristics representative of the dynamics of the region can also be obtained from continued processing of the static octodimensional vectors of characteristics that are received by the electronic system for a given region. Thus, it is not necessary to use a database since the static octodimensional vectors of characteristics associated with the region do not need to be stored.

In order to check the proper operation of the invention, a series of tests has been conducted in a test channel intended to simulate an environment similar to the one that can be found in the marine environment so that these tests are as representative as possible. It is important to emphasize that this test channel allows various weather conditions to be simulated.

The most important technical characteristics of the test channel are the following:

The channel is 6 meters long, 1.2 meters wide and 1.3 meters high;
It is made of stainless steel;
It is provided with a pump allowing recirculation of water in the channel so that its homogenization is achieved;
It has a removable central partition which purpose is to restrict the test surface and to facilitate cleaning;
It is provided with two resistors at the ends thereof to heat the water within the channel, these resistors being controllable automatically;
It is provided with a glycol cooler to achieve the cooling of water within the channel, this cooler receiving water diverted by the above mentioned recirculation pump;
It is provided with a wave generator comprising basically a piston-driven metal blade, with the speed being adjustable;
It is provided with two fans, one being fixed and the other being movable, intended for wind generation, the intensity of which is controlled by a frequency converter;
It is provided with two halogen lights, one being fixed and the other being movable, to simulate sunlight reflections;
It is provided with a number of sprinklers to simulate rain, whose intensity can be regulated by means of a valve;
It is provided with a gutter along the channel which, once filled with water and dry ice ($CO_2$), fog is generated, its intensity being adjustable from the amount of dry ice used;
It is provided with an infrared camera, mounted on a top platform with reference to the channel arranged approximately 2.5 meters from the water surface (minimum focus distance of 2.1 meters), which also allows the angle of incidence to be varied with respect to water surface;
It is provided with a stand-alone sensor allowing air temperature to be adjusted between 18 and 30° C. approximately.

The infrared camera used is, for example, a model SR-340, T18057 camera available from FLIR.

Test results are shown in FIGS. 7 to 11, which are obtained from recordings of hydrocarbon spill in the tank under different situations. In these figures, the image (a) shows the frame obtained from the video file generated by the infrared camera; the image (b) represents the image after being pre-processed; the image (c) represents the image after being segmented; and image (d) shows the selection of the region(s) classified as spill.

Figure 7:
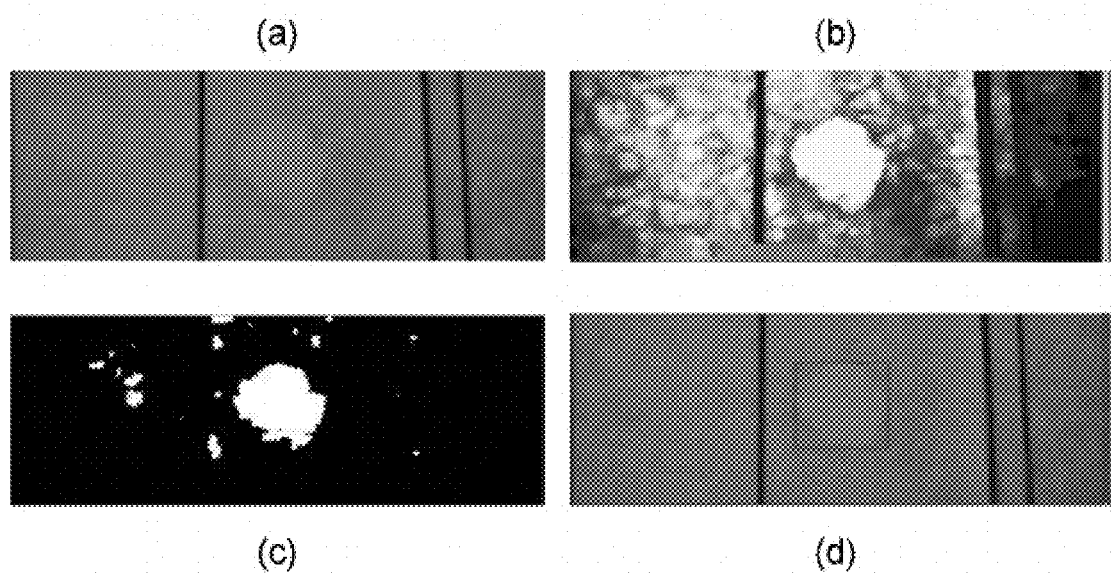
FIG. 7 shows different images representing the evolution of one image of the surface of an aqueous medium obtained by an infrared camera, in a first test, during which the method according to the invention shown in FIG. 1 is executed.

The results are as follows:

Test 1
Test Conditions:
Type of hydrocarbon: Lubina
Amount of hydrocarbon: 1 ml
Water temperature: 24.4° C.
Room temperature: 18.7° C.
Wind: weak wind
Fog: no fog
Rain: no rain Under these conditions, and as shown in FIG. 7, the invention performs a correct detection of the spot, with other small items that may be due to water currents being discarded.

Figure 8:
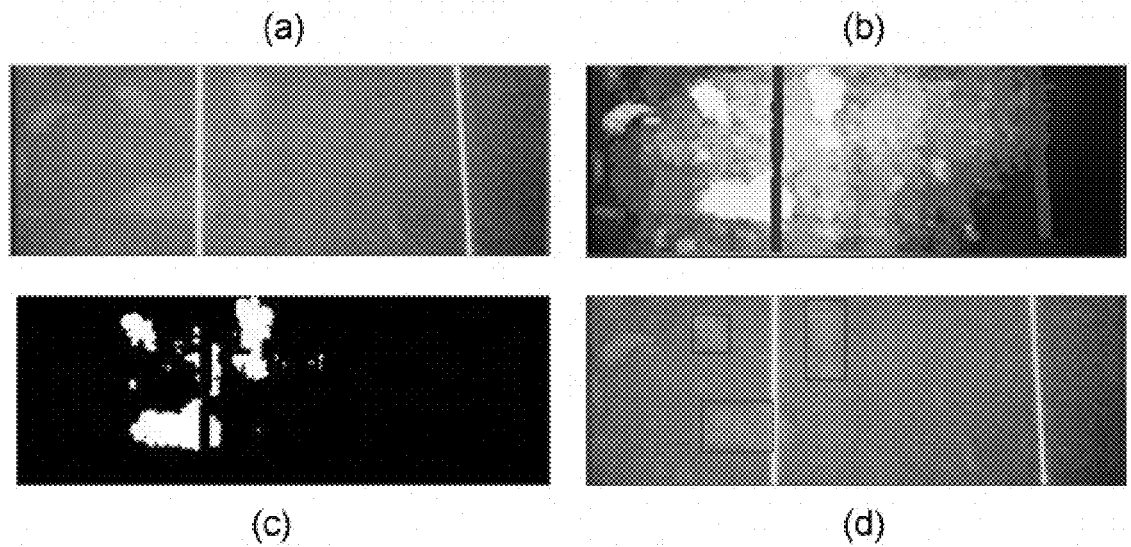
FIG. 8 shows different images representing the evolution of an image of the surface of an aqueous medium obtained by an infrared camera, in a second test, during which the method according to the invention shown in FIG. 1 is executed.

Test 2
Test Conditions:
Type of hydrocarbon: Lubina
Amount of hydrocarbon: 1 ml
Water temperature: 27° C.
Room temperature: 22° C.
Wind: no wind
Fog: no fog
Rain: no rain Under these conditions, and as shown in FIG. 8, different spots having an area larger than the established threshold are observed.

Figure 9:
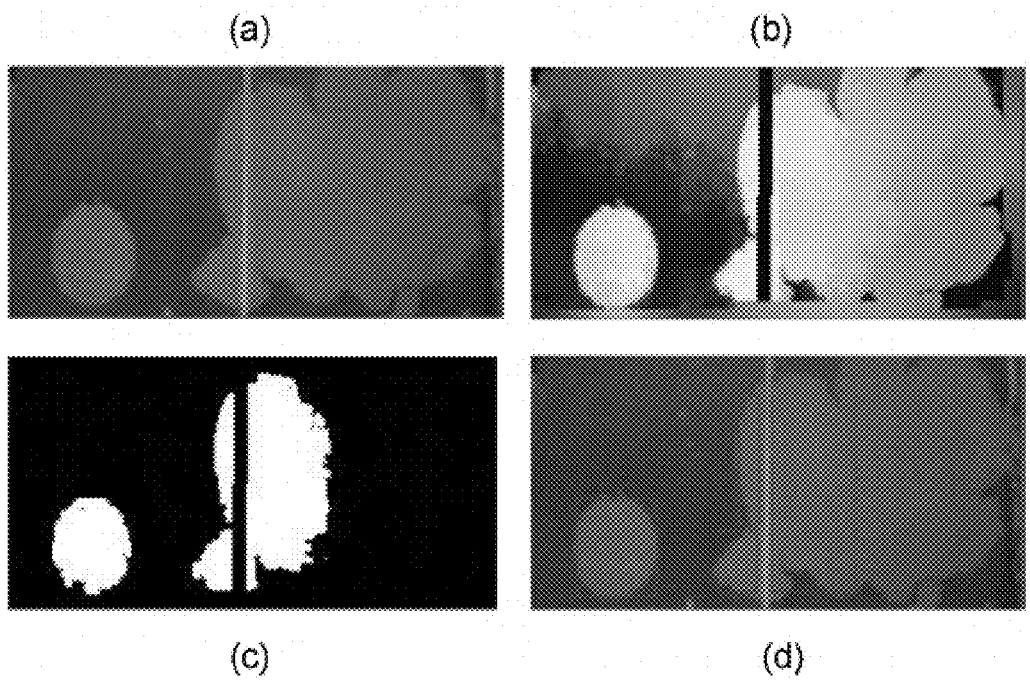
FIG. 9 shows different images representing the evolution of an image of the surface of an aqueous medium obtained by an infrared camera, in a third test, during which the method according to the invention shown in FIG. 1 is executed.

Test 3
Test Conditions:
Type of hydrocarbon: Lubina
Amount of hydrocarbon: 1 ml
Water temperature: 19.5° C.
Room temperature: 19.6° C.
Wind: 5 m/s
Fog: no fog
Rain: no rain Under these conditions, and as shown in FIG. 9, the two spots are correctly detected. Both spots have an area larger than the established threshold.

Test 4

Figure 10:
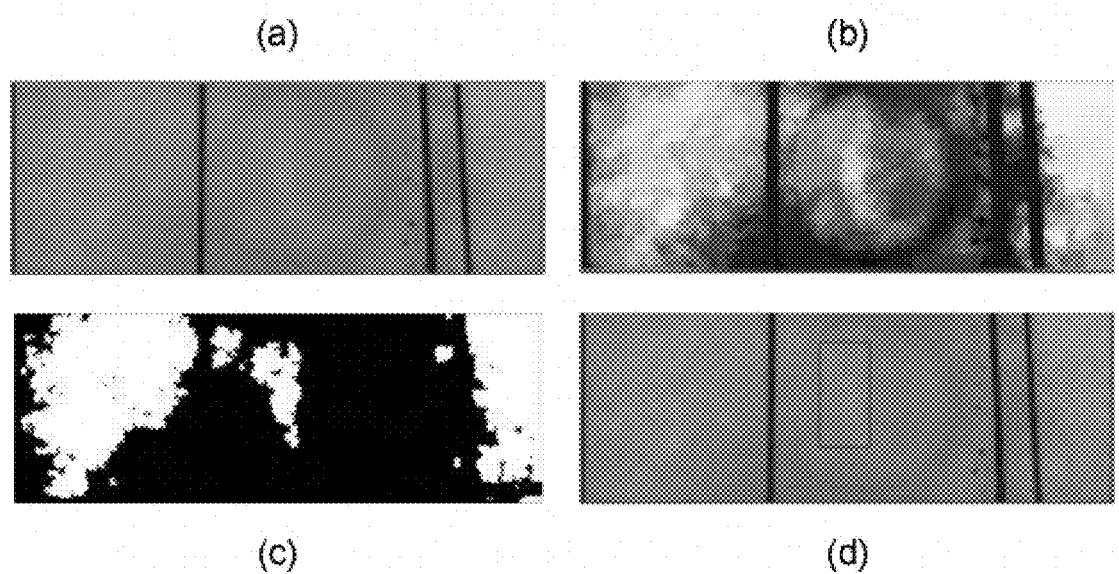
FIG. 10 shows different images representing the evolution of an image of the surface of an aqueous medium obtained by an infrared camera, in a fourth test, during which the method according to the invention shown in FIG. 1 is executed.

Test Conditions:
Type of hydrocarbon: Lubina
Amount of hydrocarbon: 1 ml
Water temperature: 29.5° C.
Room temperature: 20° C.
Wind: no wind
Fog: fog
Rain: no rain Under these conditions, and as shown in FIG. 10, the spot in the centre of the tank in the presence of fog is detected.

Test 5

Figure 11:
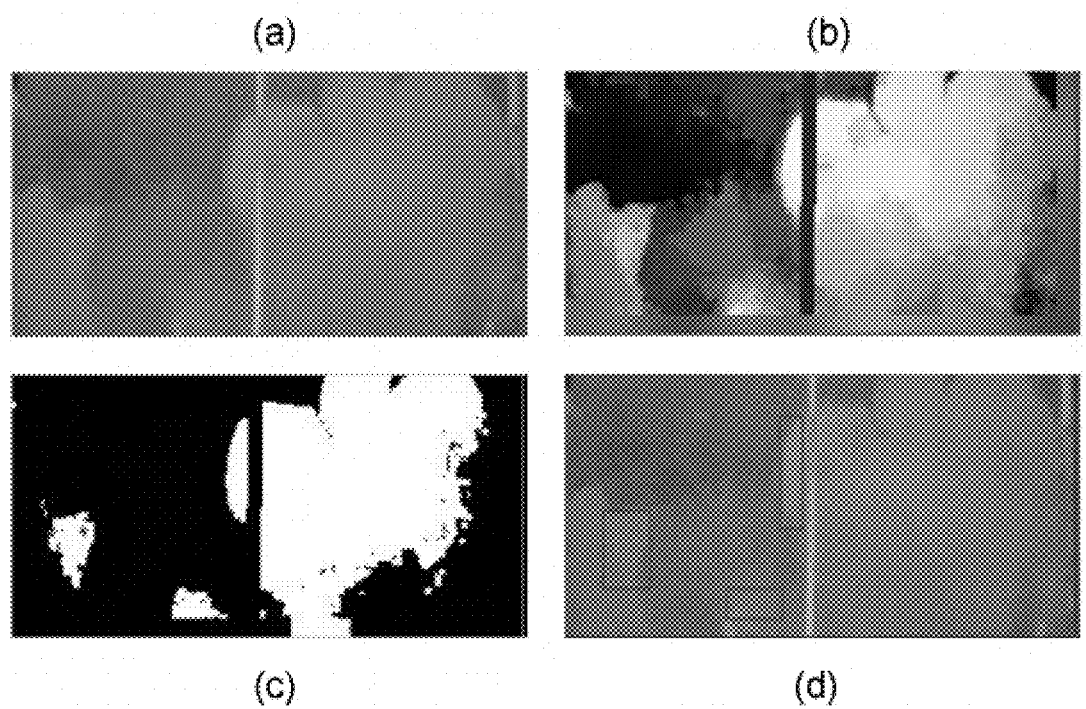
FIG. 11 shows different images representing the evolution of an image of the surface of an aqueous medium obtained by an infrared camera, in a fifth test, during which the method according to the invention shown in FIG. 1 is executed.
Figure 12:
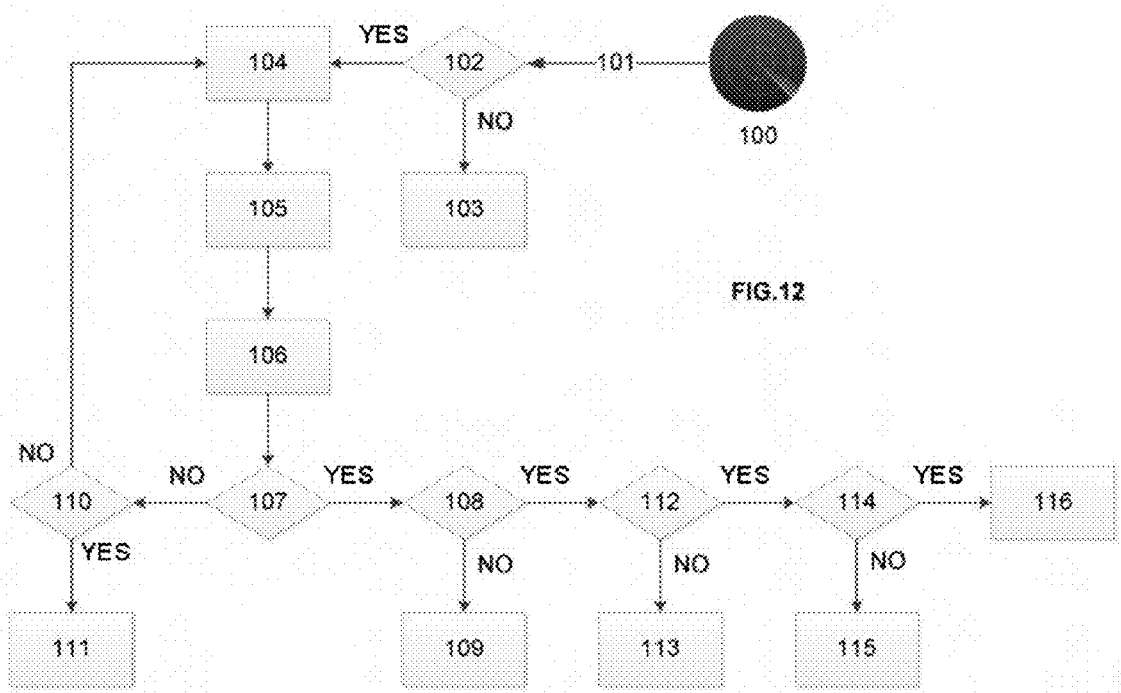
FIG. 12 shows a flowchart of the method for detecting spill according to the invention when a radar and an infrared camera are used as sensors.

Test Conditions:
Type of hydrocarbon: Lubina
Amount of hydrocarbon: 1 ml
Water temperature: 18.3° C.
Room temperature: 19° C.
Wind: no wind
Fog: no fog
Rain: rain Under these conditions, and as shown in FIG. 11, spots are detected while they are not completely dispersed. In this case it is important to note that the test was performed by depositing the crude into the tank and then activating the rain.

A further possible embodiment of the invention refers to the combination of an infrared camera and a radar where two different sensors based on different principles are provided, which has important advantages:

Increased operability (operating hours per year);
Less chance of false alarms.

The radar is a sensor capable to identifying changes in surface roughness, while the infrared camera is capable of detecting differences of the substances in terms of thermal and emissivity. Emissivity is a property of the substances that affect the contrast of the image captured with an infrared camera. It is known in the prior art that emissivity differences between hydrocarbon and water are significant which facilitates detection of the hydrocarbon in water.

The basic operation of the invention is as follows.

If weather conditions are favourable, the radar acts as the primary sensor, continuously monitoring the area of interest in the sea surface and generating videos which are subsequently analysed through the radar interpretation algorithm. The output of this algorithm is a signal indicating that a spill is present or not.

If weather conditions are not favourable, i.e., they prevent the surface conditions from being detected by the radar, the infrared camera acts as the sole sensor for automatic monitoring of the area, generating videos which are subsequently processed as described above, with warning signals being generated in case of detecting a spill.

In case that the output 101 of the interpretation algorithm 100 of the radar is a signal indicative of spill, it is checked 102 whether there is an infrared camera capable of monitoring the spill. In case of negative result in checking, a warning signal of spill is directly generated 103, since there is no camera capable of monitoring the area. At this point it is important to note that when a spill is detected by the radar interpretation algorithm 100, the signal indicative of spill is not only generated but data about the spill is also sent, such as the geographical position of the spill, its shape, or size or extent.

In case of positive result in checking, the infrared camera is positioned 104 for properly capturing images (usually in the form of video file or real time video signal) of the area of sea surface where spill could have been produced considering information on the geographical position provided by the radar interpretation algorithm.

The video file or the video signal captured by the infrared camera is sent 105 to the camera interpretation algorithm, as described above, to determine 106 whether a spill has really been produced. Therefore, it should be checked 107 whether the output signal of the camera interpretation algorithm is indicative of spill. In case of positive result, it is checked 108 whether the radar is operating and in case of negative result, a warning signal of spill is generated 109 solely based on detection carried out by the infrared camera interpretation algorithm.

In case of negative result in checking on whether the output signal of the camera interpretation algorithm is indicative of spill, it is checked 110 whether there was a previous detection by the radar. In case of positive result, it is not possible to generate 111 an alarm without a spill being confirmed by the camera interpretation algorithm. In case of negative result, the camera 104 is arranged again for obtaining new images on the area of the sea surface in which spill could have been produced.

In case of positive result on whether the radar is operating, it is checked 112 whether there have been a previous detection of spill by the radar. In case of negative result it is not possible to generate a warning signal 113 with confirmation of the radar. In case of positive result, it is checked 114 whether spill has been located by the infrared camera interpretation algorithm at the location indicated by the radar. In case of negative result, it is not possible to generate a warning signal 115. In case of positive result, a warning signal is generated 116 as the spill has been confirmed by both the radar interpretation algorithm and the infrared camera interpretation algorithm.

From what is herein described, it is important to note that it is also possible to combine the described system (radar+infrared camera) with other sensors such as visible cameras, ultraviolet cameras or laser fluorosensors.

Although one particular embodiment of the present invention has been depicted and described, it is evident that those skilled in the art will be able of providing changes and modifications, or replacing the details with other technically equivalent without departing from the scope of protection defined by the appended claims.

Also despite the fact that the embodiments of the invention described above with reference to the drawings comprise computer systems and processes performed in computer systems, the invention also extends to computer programs, more particularly computer programs in or on a carrier, adapted to practice the invention. The computer program may be in the form of source code, object code or intermediate code between source code and object code, such as in a partially compiled form, or in any other desirable form suitable to be used in implementing the processes according to the invention. The carrier may be any entity or device capable of carrying the program.

For example, the carrier may comprise a storage medium such as a ROM, for example a CD ROM or a semiconductor ROM, or a magnetic recording medium, e.g. a floppy disc or a hard disk. In addition, the carrier may be a transmissible carrier such as an electrical or optical signal that can be transmitted through an electrical or optical cable or by radio or other means.

When the computer program is contained in a signal that can be transmitted directly through a cable or other device or means, the carrier may be composed of such cable or other device or means.

Alternatively, the carrier may be an integrated circuit in which the computer program is embedded, said integrated circuit being adapted to perform, or to be used in carrying out, the relevant processes.

The invention claimed is:

1. A method for detecting hydrocarbon spill in an aqueous medium from a plurality of images of the surface of the aqueous medium obtained by an infrared camera, comprising:
   analyzing one image of the plurality of images of the surface of the aqueous medium, wherein the analyzing of the one image comprises:
      segmenting the image of the surface of the aqueous medium in order to split the image into static regions, and
      obtaining a multidimensional vector of characteristics representative of each of the static regions;
   checking whether at least one of the static regions could be identified as a hydrocarbon spill;
   in case of a positive result in the checking,
      assessing whether a point representing the multidimensional vector of characteristics representative of the static region is within a reference zone defined in a multidimensional space, this reference zone being representative of multidimensional vectors of characteristics of regions corresponding to actual hydrocarbon spills in the aqueous medium; and
         if it is determined that the point representing the multidimensional vector of characteristics representative of the static region is within the reference zone, generating a warning signal of hydrocarbon spill in the aqueous medium.

2. The method of claim 1, wherein the analyzing of the one image of the plurality of images of the surface of the aqueous medium further comprises
   conditioning the image of the surface of the aqueous medium;
   and wherein the segmenting the image of the surface of the aqueous medium comprises:
      segmenting the conditioned image.

3. The method of claim 2, wherein the conditioning the image of the surface of the aqueous medium comprises:
   reducing noise in the image of the surface of the aqueous medium; and
   correcting for variations in an image intensity due to differences in an angle of an infrared camera relative to the surface of the aqueous medium.

4. The method of claim 3, wherein the conditioning of the image of the surface of the aqueous medium further comprises:
   detecting the aqueous medium in the image.

5. The method of claim 1, wherein
   in the case of a positive result in the checking,
      checking whether the static region was previously entered into a data repository relating to areas that could be identified as a hydrocarbon spill in the aqueous medium, this repository comprising an identifier for each previously entered region and a corresponding multidimensional vector of characteristics for the region; and
   in case of a negative result in the checking,
      entering an identifier for the static region and the corresponding multidimensional vector of characteristics obtained from the static region into the data repository for the analyzed image; and
   in the case of the positive result in the checking,
      entering the multidimensional vector of characteristics into a portion of the data repository associated with the identifier for the static region; and
      generating a multidimensional vector of characteristics representative of dynamics of the static region from the multidimensional vector of characteristics associated with the identifier for the static region;
      wherein the multidimensional vector of characteristics associated with the static region is the generated multidimensional vector of characteristics representative of the dynamics of the region.

6. A non-transitory computer readable medium storing instructions for causing a computer system to execute the method for detecting hydrocarbon spill in an aqueous medium from a plurality of images of the surface of the aqueous medium obtained by an infrared camera as claimed in claim 1.

7. A method for detecting hydrocarbon spill on the surface of an aqueous medium, comprising:
   receiving a warning signal of detection of hydrocarbon spill in the aqueous medium generated from at least one image obtained by a radar;
   checking whether there is an infrared camera capable of monitoring the spill;
   in case of a negative result,
      generating a warning signal of detection of hydrocarbon spill in the aqueous medium from the warning signal of detection generated from the at least one image obtained by a radar;
   in case of a positive result,
      executing the method for detecting hydrocarbon spill in the aqueous medium from a plurality of images of the surface of the aqueous medium obtained by an infrared camera as claimed in claim 1.

8. The method of claim 7, wherein in case of the positive result in checking whether there is an infrared camera capable of monitoring the spill, the method further comprises
   positioning the infrared camera.

9. The method of claim 7, wherein the method further comprises:
   receiving a geographical position of the spill in the aqueous medium; and
   wherein checking whether there is an infrared camera capable of monitoring the spill comprises checking whether there is an infrared camera capable of monitoring the surface of the aqueous medium that is in the received geographical position.

10. A non-transitory computer readable medium storing instructions for causing a computer system to execute the method for detecting hydrocarbon spill in an aqueous medium as claimed in claim 7.

11. An electronic system for detecting hydrocarbon spill in an aqueous medium from a plurality of images of the surface of the aqueous medium obtained by an infrared camera, comprising:
   electronic means for analyzing an image of the plurality of images of the surface of the aqueous medium, wherein the analyzing of the one image comprises:
      electronic means for segmenting the image of the surface of the aqueous medium in order to split the image into static regions; and electronic means for obtaining a multidimensional vector of characteristics representative of each of the static region;

electronic means for checking whether at least one of the static regions could be identified as a hydrocarbon spill;

in case of a positive result in the checking, electronic means for providing the multidimensional vector of characteristics representative of the static region;

electronic means for assessing whether a point representing the multidimensional vector of characteristics associated with the static region is within a reference zone defined in a multidimensional space, this reference zone being representative of multidimensional vectors of characteristics of regions corresponding to actual hydrocarbon spills in an aqueous medium; and electronic means for generating a warning signal of hydrocarbon spill in the aqueous medium, wherein if it is determined that the point representing the multidimensional vector of characteristics representative of the static region is within the reference zone a warning signal is generated.

12. A computer system for detecting hydrocarbon spill in an aqueous medium, comprising:

an infrared camera adapted for obtaining a plurality of images of the surface of the aqueous medium;

a memory and a processor containing instructions stored in the memory and executable by the processor, the instructions comprising functionality for:

analyzing one image of the plurality of images of the surface of the aqueous medium obtained by the infrared camera, wherein the analyzing of the one image comprises:

segmenting the image of the surface of the aqueous medium in order to split the image into static regions;

obtaining a multidimensional vector of characteristics representative of each of the static regions;

checking whether at least one of the static regions could be identified as a hydrocarbon spill; and in case of a positive result in the checking, providing the multidimensional vector of characteristics representative of the static region;

assessing whether a point representing the multidimensional vector representative of the static region is within a reference zone defined in a multidimensional space, this reference zone being representative of multidimensional vectors of characteristics of regions corresponding to actual hydrocarbon spills in an aqueous medium; and if it is determined that the point representing the multidimensional vector of characteristics representative of the static region is within the reference zone, generating a warning signal of hydrocarbon spill in the aqueous medium.

13. An electronic system for detecting hydrocarbon spill on the surface of an aqueous medium, comprising:

electronic means for receiving a warning signal of detection of hydrocarbon spill in the aqueous medium generated from at least one image obtained by a radar;

electronic means for checking whether there is an infrared camera capable of monitoring the spill; and in case of a negative result, electronic means for generating a warning signal of hydrocarbon spill in the aqueous medium;

in case of a positive result, electronic means for executing the method for detecting hydrocarbon spill in an aqueous medium from a plurality of images of the surface of the aqueous medium obtained by an infrared camera as claimed in claim 1.

14. A computer system for detecting hydrocarbon spill on the surface of an aqueous medium, comprising:

at least one radar;

at least one infrared camera; and a memory and a processor containing instructions stored in the memory and executable by the processor, the instructions comprising functionality for:

receiving a warning signal of detection of hydrocarbon spill in the aqueous medium generated from at least one image obtained by the radar;

checking whether there is an infrared camera capable of monitoring the spill; and in case of a negative result, generating a warning signal of hydrocarbon spill in the aqueous medium;

in case of a positive result, executing the method for detecting hydrocarbon spill in an aqueous medium from a plurality of images of the surface of the aqueous medium obtained by an infrared camera as claimed in claim 1.

* * * * *